(12) United States Patent
Giannakopulos

(10) Patent No.: US 11,688,594 B2
(45) Date of Patent: Jun. 27, 2023

(54) MASS SPECTROMETER AND METHOD OF MASS SPECTROMETRY

(71) Applicant: Thermo Fisher Scientific (Bremen) GmbH, Bremen (DE)

(72) Inventor: Anastassios Giannakopulos, Bremen (DE)

(73) Assignee: Thermo Fisher Scientific (Bremen) GmbH, Bremen (DE)

(*) Notice: Subject to any disclaimer, the term of this patent is extended or adjusted under 35 U.S.C. 154(b) by 77 days.

(21) Appl. No.: 17/524,683

(22) Filed: Nov. 11, 2021

(65) Prior Publication Data
US 2022/0157584 A1 May 19, 2022

(30) Foreign Application Priority Data
Nov. 16, 2020 (GB) .................................. 2017995

(51) Int. Cl.
*H01J 49/00* (2006.01)
*G01N 30/86* (2006.01)
*G01N 33/68* (2006.01)
*G01N 30/72* (2006.01)

(52) U.S. Cl.
CPC ...... *H01J 49/0031* (2013.01); *G01N 30/8631* (2013.01); *G01N 33/6848* (2013.01); *H01J 49/005* (2013.01); *H01J 49/0045* (2013.01); *G01N 30/7266* (2013.01)

(58) Field of Classification Search
CPC .. H01J 49/0031; H01J 49/005; H01J 49/0027; H01J 49/004; H01J 49/10; H01J 49/40; H01J 49/06; H01J 49/26; H01J 49/0045; G01N 30/8631; G01N 30/7266; G01N 30/72; G01N 33/6848; G01N 27/62
USPC ........................................................ 250/282
See application file for complete search history.

(56) References Cited

U.S. PATENT DOCUMENTS

2005/0098721 A1* 5/2005 Bateman ............. H01J 49/0031
250/282
2014/0131567 A1 5/2014 Makarov

* cited by examiner

*Primary Examiner* — Kiet T Nguyen (57) ABSTRACT

A method of mass spectrometry for analyzing a sample within a mass range of interest includes the steps: ionizing the sample to produce a plurality of precursor ions; performing an MS1 scan of the precursor ions comprising mass analyzing the precursor ions across the mass range of interest, to obtain an MS1 mass spectrum of the precursor ions; determining ion intensity values within the MS1 mass spectrum; selecting precursor mass segments within the mass range of interest, and for each precursor mass segment: fragmenting the precursor ions within that precursor mass segment; and performing an MS2 scan of the fragmented ions by: controlling an amount of fragmented ions for that precursor mass segment, based on an intensity value for that precursor mass segment derived from the MS1 spectrum; and mass analyzing the amount of fragmented ions.

15 Claims, 6 Drawing Sheets

MASS SPECTROMETER AND METHOD OF MASS SPECTROMETRY

FIELD OF THE INVENTION

The present invention relates to mass spectrometry of organic and in particular biological samples such as proteins, peptides, metabolites, lipids and the like.

In particular, it relates to a high-resolution identification and quantification technique with applications in proteomics, metabolomics, lipidomics, and so forth.

BACKGROUND OF THE INVENTION

Mass spectrometry is a long-established technique for identification and quantitation of often complex mixtures of large organic molecules. In recent years, techniques have been developed that allow analysis of a wide range of both biological and non-biological materials, with application across the fields of law enforcement (e.g. identification of drugs and explosives materials), environmental, scientific research, and biology (e.g. in proteomics, the study of simple and complex mixtures of proteins, with applications in drug discovery, disease identification and so forth).

Proteins, comprising large numbers of amino acids, are typically of significant molecular weight. Thus, accurate identification and quantitation of the protein by direct mass spectrometric measurement is challenging. It is thus well known to carry out fragmentation of the precursor sample material. A variety of fragmentation techniques are known, which may result in the generation of different fragment ions from the precursor ions. Moreover, the fragmentation mechanism may be affected by different applied fragmentation energies.

To determine the molecular structure of sample molecules, a mass spectrometer is first used to mass analyze all sample ions (precursor ions) within a selected window of mass to charge ratio (m/z). Such a scan is often denoted as an MS1 scan. The selected sample ions are then fragmented and the resulting fragments are subsequently mass analyzed across the selected m/z range. The scan of the fragmented ions is often denoted as an MS2 scan.

Analysis of samples can broadly be separated into data independent analysis/acquisition (DIA) and data dependent analysis/acquisition (DDA) techniques. DIA seeks to determine what is present in a sample of potentially unknown identity.

DDA seeks to confirm that one or more species is/are present in a given sample. Methods of DDA identify a fixed number of precursor ion species, and select and analyze those via mass spectrometry using MS2 scans. The determination of which precursor ion species are of interest in DDA may be based upon intensity ranking (for example, the top ten most abundant species as observed by peaks in a MS1 spectrum"), or by defining an "inclusion list" of precursor mass spectral peaks (for example by user selection), from which MS2 spectra are always acquired regardless of the intensity ranking of the peak in the MS1 mass spectrum. Still otherwise, an "exclusion list" of peaks in MS1 can be defined, for example by a user, based e.g. on prior knowledge of the expected sample contents.

DIA avoids the decisions necessary in DDA, by simply dividing the mass range of interest (typically user defined) into segments and obtaining MS2 spectra for each segment. With traditional DIA, the acquisition of an MS1 precursor spectrum becomes more or less optional, since the parameters of the selection window for the sample ions carries information about the range of possible sample ions within that window.

Over the entire spectrum of the MS1 scan, i.e. of precursor masses, the ion intensities can vary significantly (e.g. by several orders of magnitude), such that a high dynamic range is required in order to detect both high intensities and very low ion intensities.

It is an object of the invention to address the dynamic range problem in mass spectrometry, in particular in data-independent mass spectrometry.

SUMMARY OF THE INVENTION

The present invention provides a method of mass spectrometry according to claim 1, a mass spectrometer in accordance with claim 14 and a computer program product of claim 16. Advantageous modifications can be made in accordance with the dependent claims.

According to the present invention, a method of mass spectrometry for analyzing a sample within a mass range of interest may be provided. The method comprises the steps:
  ionizing the sample to produce a plurality of precursor ions;
  performing an MS1 scan of the precursor ions comprising mass analyzing the precursor ions across the mass range of interest, to obtain an MS1 mass spectrum of the precursor ions;
  determining ion intensity values within the MS1 mass spectrum;
  selecting precursor mass segments within the mass range of interest, each precursor mass segment having a mass range, and for each precursor mass segment:
    fragmenting the precursor ions within that precursor mass segment; and
    performing an MS2 scan of the fragmented ions by:
      controlling an amount of fragmented ions for that precursor mass segment, based on an intensity value for that precursor mass segment derived from the MS1 spectrum; and
      mass analyzing the amount of fragmented ions.

The amount of fragmented ions may be controlled by controlling the injection time of the fragmented ions for accumulating an ion packet from the fragmented ions within an extraction trap and wherein performing the MS2 scan includes ejecting the ion packet from the extraction trap into a mass analyzer for performing the MS2 scan.

In that context, the injection time may be determined, such that a total charge or a number of fragmented ions is substantially equal for ion packets of each of the precursor mass segments.

The amount of ions may be controlled by controlling the number of pulses generated from the fragmented ions within the precursor mass segment by an ion injector, preferably an orthogonal accelerator injector, the pulses being injected by the ion injector into a time-of-flight mass analyzer for generating the MS2 scan.

A plurality of intensity classes may be defined for the intensity values, and wherein each of the precursor mass segments is assigned to one of the plurality of intensity classes, and wherein the amount of fragmented ions is controlled based on the assigned intensity class.

In that context, an order of processing the precursor mass segments may be defined based on the intensity classes, preferably such that a precursor mass segment assigned to an intensity class associated with a higher intensity value is processed before a precursor mass segment assigned to an intensity class associated with a lower intensity value.

A plurality of mass subranges, each mass subrange comprising a plurality of neighboring precursor mass segments, are defined within the mass range of interest, such that all the precursor mass segments within a mass subrange are assigned to the same intensity value.

Intensity peaks may be identified within the mass range of interest and the intensity values may comprise peak intensity values of the identified intensity peaks.

Each of the plurality of precursor mass segments may have substantially the same mass range, and preferably wherein the mass range is 20 Da (Dalton) or less, 15 Da (Dalton) or less, 10 Da (Dalton) or less, 8 Da (Dalton) or less, 6 Da (Dalton) or less, 4 Da (Dalton) or less, 3 Da (Dalton) or less, or 2 Da (Dalton) or less.

The precursor mass segments may comprise precursor mass segments that are adjacent to each other and non-overlapping.

Mass ranges of precursor mass segments may or may not be overlapping.

For performing the MS1 scan and for performing the MS2 scan the same mass analyzer may be used, and wherein preferably the mass analyzer is a time-of-flight mass analyzer.

The MS1 scan may be performed using a first mass analyzer, and the MS2 scan may be performed using a second mass analyzer, and wherein preferably the first mass analyzer is a Fourier transform mass analyzer, more preferably an Orbitrap mass analyzer, and wherein preferably the second mass analyzer is a time-of-flight mass analyzer, more preferably a multi-reflection time-of-flight mass analyzer.

In accordance with the present teachings, a mass spectrometer for performing mass spectrometry on a sample across a mass range of interest may be provided. The mass spectrometer comprises:

an ionization source for producing a plurality of precursor ions from the sample provided by a chromatography system;

a mass selector for selecting a mass range of the precursor ions;

a mass analyzer for performing an MS1 scan of the precursor ions in the MS1 domain;

a fragmentation apparatus;

a mass analyzer for performing an MS2 scan of fragmented ions in the MS2 domain; an ion packet or ion pulse forming apparatus, and a controller configured to:

(i) cause the mass selector to select precursor ions within the mass range of interest, (ii) cause the mass analyzer for performing an MS1 scan to perform an MS1 scan of the precursor ions within the mass range of interest to obtain a MS1 spectrum of the precursor ions in the MS1 domain, (iii) determine ion intensity values within the MS1 spectrum;

(iv) cause the mass selector to select within the mass range of interest a plurality of precursor mass segments, each precursor mass segment having a mass range (v) control an amount of fragmented ions for each precursor mass segment, based on an intensity value for that precursor mass segment derived from the MS1 spectrum;

(vi) cause the fragmentation apparatus to fragment the precursor ions within each precursor mass segment (vii) cause the ion packet or ion pulse forming apparatus to form the amount of fragmented ions as one or more ion packets or ion pulses and to inject the ion packets or ion pulses of fragmented ions into the mass analyzer for performing an MS2 scan, (viii) cause the mass analyzer for performing an MS2 scan to mass analyze the amount of fragmented ions of the one or more ion packets or ion pulses.

In the mass spectrometer for performing mass spectrometry the controller may susceptible to the modifications of any of the methods described above.

In accordance with the present teachings, a computer program product may be provided, comprising program instructions that cause a controller of a mass spectrometer to perform any of the methods described above, when loaded into a memory of the controller.

DETAILED DESCRIPTION OF EMBODIMENTS

The invention may be put into practice in a number of ways and specific embodiments will now be described by way of example only and with reference to the drawings. It will be appreciated that the invention is not limited to the embodiments that are described and that some embodiments may not include all of the features that are described below. It will be evident, however, that various modifications and changes may be made herein without departing from the broader scope of the invention as set forth in the claims.

Herein the term mass may be used to refer to the mass-to-charge ratio, m/z. The resolution of a mass analyzer is to be understood to refer to the resolution of the mass analyzer as determined at a mass-to-charge ratio of 200 unless otherwise stated. An intensity value in a mass spectrum may be expressed variously as ion abundance or peak height etc.

Figure 1:
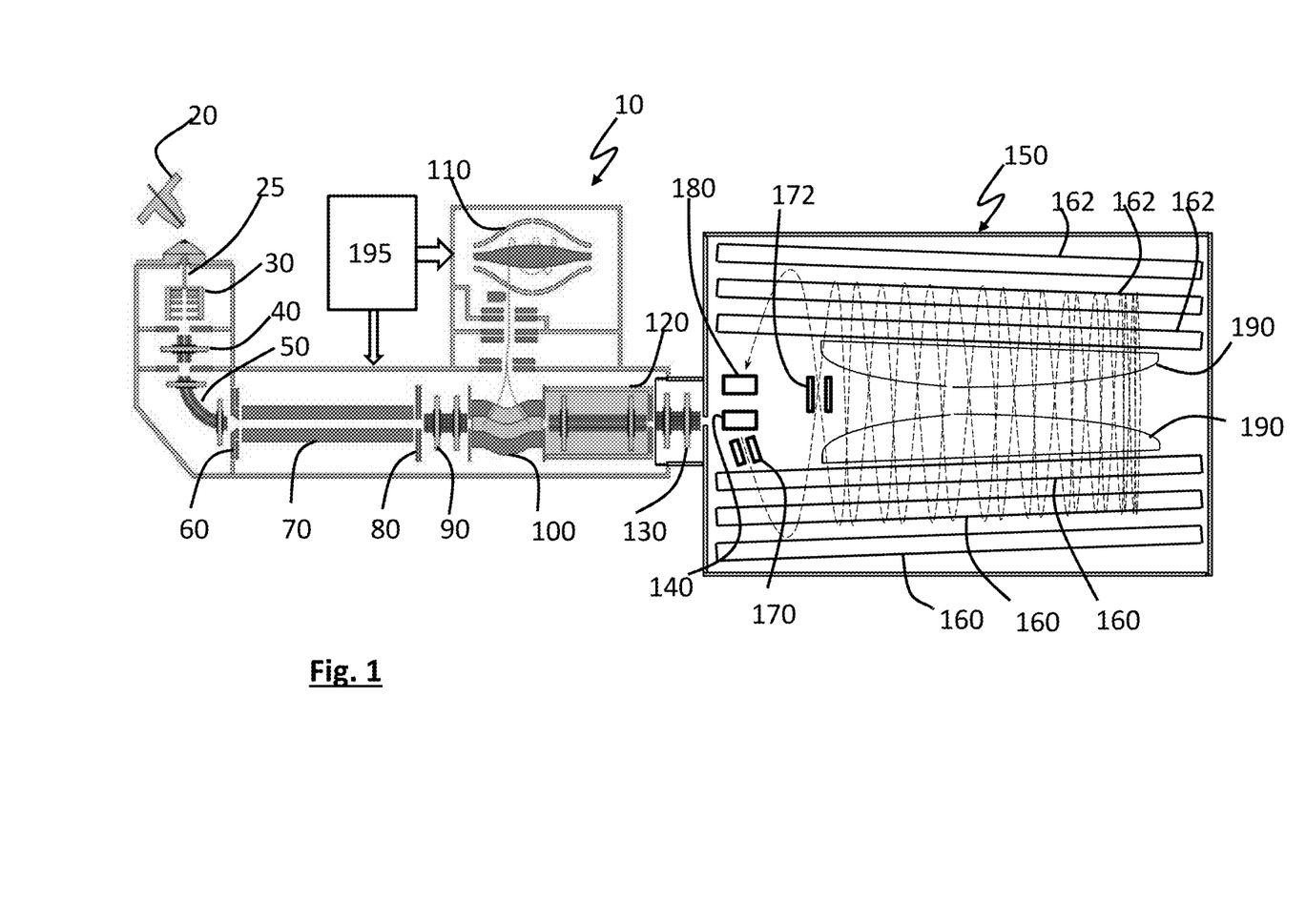
FIG. 1 shows a schematic diagram of a mass spectrometer suitable for carrying out the present invention.

FIG. 1 shows a schematic arrangement of a mass spectrometer 10 suitable for carrying out methods in accordance with embodiments of the present invention.

In FIG. 1, a sample to be analyzed is supplied (for example from an autosampler) to a chromatographic apparatus such as a liquid chromatography (LC) column (not shown in FIG. 1). One such example of an LC column is the Thermo Fisher Scientific, Inc ProSwift™ monolithic column which offers high performance liquid chromatography (HPLC) through the forcing of the sample carried in a mobile phase under high pressure through a stationary phase of irregularly or spherically shaped particles constituting the stationary phase. In the HPLC column, sample molecules elute at different rates according to their degree of interaction with the stationary phase.

The sample may contain molecules selected from one or more of: biopolymers, proteins, peptides, polypeptides, amino acids, carbohydrates, sugars, fatty acids, lipids, vitamins, hormones, polysaccharides, phosphorylated peptides, phosphorylated proteins, glycopeptides, glycoproteins, oligionucleotides, oligionucleosides, DNA, fragments of DNA, cDNA, fragments of cDNA, RNA, fragments of RNA, mRNA, fragments of mRNA, tRNA, fragments of tRNA, monoclonal antibodies, polyclonal antibodies, ribonucleases, enzymes, metabolites, and/or steroids. The sample may comprise at least 2, 5, 10, 20, 50, 100, 500, 1000, or 5000 different molecules.

A chromatograph may be produced by measuring over time the quantity of sample molecules which elute from the HPLC column using a detector (for example a mass spectrometer). Sample molecules which elute from the HPLC column will be detected as a peak above a baseline measurement on the chromatograph. Where different sample molecules have different retention times, a plurality of peaks on the chromatograph may be detected. Preferably, individual sample peaks are separated in time from other peaks in the chromatogram such that different sample molecules do not interfere with each other. On a chromatograph, a presence of a chromatographic peak corresponds to a time period over which the sample molecules are present at the detector. As such, a width of a chromatographic peak is equivalent to a time period over which the sample molecules are present at a detector. Preferably, a chromatographic peak has a Gaussian shaped profile, or can be assumed to have a Gaussian shaped profile. Accordingly, a width of the chromatographic peak can be determined based on a number of standard deviations calculated from the peak. For example, a peak width may be calculated based on 4 standard deviations of a chromatographic peak. Alternatively, a peak width may be calculated based on the width at half the maximum height of the peak. Other methods for determining the peak width known in the art may also be suitable.

The sample molecules thus separated via liquid chromatography are then ionized using an electrospray ionization source (ESI source) 20 which is at atmospheric pressure. Sample ions then enter a vacuum chamber of the mass spectrometer 10 and are directed by a capillary 25 into a lens 30 that may be embodied as an RF-only S lens 30 or as a lens 30 that applies a combination of RF and DC that propels ions forward. The lens 30 may apply a stack of rings of progressively decreasing diameter, on which a forward driving DC potential may be applied. The ions are focused by the lens 30 into an injection multipole 40 which injects the ions into a bent multipole 50 with an axial field. The bent multipole 50 guides (charged) ions along a curved path through it whilst unwanted neutral molecules such as entrained solvent molecules are not guided along the curved path and are lost.

An ion gate (TK lens) 60 is located at the distal end of the bent multipole 50 and controls the passage of the ions from the bent multipole 50 into a downstream mass selector in the form of a quadrupole mass filter 70. The quadrupole mass filter 70 is typically but not necessarily segmented and serves as a band pass filter, allowing passage of a selected mass number or limited mass range whilst excluding ions of other mass to charge ratios (m/z). The mass filter can also be operated in an RF-only mode in which it is not mass selective, i.e. it transmits substantially all m/z ions. For example, the quadrupole mass filter 70 may be controlled by a controller 195 to select a range of mass to charge ratios of the precursor ions which are allowed to pass, whilst the other ions in the precursor ion stream are filtered. Alternatively, the lens 30 may be operated as an ion gate and the ion gate (TK lens) 60 may be a static lens.

Although a quadrupole mass filter is shown in FIG. 1, the skilled person will appreciate that other types of mass selection devices may also be suitable for selecting precursor ions within the mass range of interest. For example, an ion separator as described in USA-2015287585, an ion trap as described in WO-A-2013076307, an ion mobility separator as described in US-A-2012256083, an ion gate mass selection device as described in WO-A-2012175517, or a charged particle trap as described in US799223, the contents of which are hereby incorporated by reference in their entirety. The skilled person will appreciate that other methods selecting precursor ions according to ion mobility, differential mobility and/or transverse modulation may also be suitable.

The isolation of a plurality of ions of different masses or mass ranges may also be performed using the method known as synchronous precursor scanning (SPS) in an ion trap. Furthermore, in some embodiments, more than one ion selection or mass selection device may be provided. For example, a further mass selection device may be provided downstream of the fragmentation chamber 120. In this way, MS3 or MSn scans can be performed if desired (typically using the TOF mass analyzer 150 for mass analysis).

Ions then pass through a quadrupole exit lens/split lens arrangement 80 and into a first transfer multipole 90. The first transfer multipole 90 guides the mass filtered ions from the quadrupole mass filter 70 into a curved linear ion trap (C-trap) 100. To measure the flow of ions, an electrometer (not shown) may be positioned adjacent (downstream or upstream) to the first transfer multipole 90. To that end, the electrometer may sample a predefined proportion of the ions passing through the first transfer multipole 90. Alternatively, the electrometer may be positioned adjacent to the point of entry of the ions into the C-trap 100. In a further alternative, the electrometer may be positioned adjacent to the point of exit of the ions from the C-trap 100. Preferably, the electrometer is positioned upstream of the fragmentation chamber 120 described hereafter. Using an electrometer positioned upstream of the fragmentation chamber 120 allows to measure the flow of precursor ions. The C-trap (first ion storage trap) 100 has longitudinally extending, curved electrodes which are supplied with RF voltages and axial trapping electrodes to which DC voltages are supplied. The result is a potential well that extends along the curved longitudinal axis of the C-trap 100. In a first mode of operation, the DC axial trapping voltages are set on the C-trap so that ions arriving from the first transfer multipole 90 are captured in the potential well of the C-trap 100, where they are cooled. The injection time (IT) of the ions into the C-trap determines the number of ions (ion population) that is subsequently ejected from the C-trap into the mass analyzer.

Cooled ions reside in a cloud towards the bottom of the potential well and are then ejected orthogonally from the C-trap towards the first mass analyzer 110. As shown in FIG. 1, the first mass analyzer is an orbital trapping mass analyzer 110, for example the Orbitrap® mass analyzer sold by Thermo Fisher Scientific, Inc. The orbital trapping mass analyzer 110 has an off center injection aperture and the ions are injected into the orbital trapping mass analyzer 110 as coherent packets, through the off center injection aperture. Ions are then trapped within the orbital trapping mass analyzer by a hyperlogarithmic electric field, and undergo back and forth motion in a longitudinal direction whilst orbiting around the inner electrode.

The longitudinal or axial (z) component of the movement of the ion packets in the orbital trapping mass analyzer is (more or less) defined as simple harmonic motion, with the angular frequency in the z direction being related to the square root of the mass to charge ratio of a given ion species. Thus, over time, ions separate in accordance with their mass to charge ratio.

Ions in the orbital trapping mass analyzer are detected by use of an image detector (outer electrode) which produces a "transient" in the time domain containing information on all of the ion species as they pass the image detector. The transient is then subjected to a Fast Fourier Transform (FFT) resulting in a series of peaks in the frequency domain. From these peaks, a mass spectrum, representing abundance/ion intensity versus m/z, can be produced. The controller 195 controls the mass analyzer 110 to acquire the detector transient signal, process the transient by FFT and produce the mass spectrum.

In the configuration described above, the sample ions (more specifically, a mass range of the sample ions within a mass range of interest, selected by the quadrupole mass filter) are analyzed by the orbital trapping mass analyzer without fragmentation. The resulting mass spectrum is denoted MS1. In accordance with the present teachings, the MS1 spectrum is analyzed to the identification of intensity peaks, which can be used to control the number of fragmented ions for each of the precursor mass segments as in the method described in accordance with FIG. 2. Preferably, the first mass analyzer performs the MS1 scans at a mass resolution of at least 15,000, at least 30,000, at least 50,000, or more preferably a high resolution of at least 75,000, at least 100,000, at least 150,000 or at least 200,000 (resolution at 200 m/z). The MS1 scans are preferably performed with 5 ppm, 4 ppm, 3 ppm or 2 ppm or better (e.g. 1-2 ppm) in mass accuracy. Preferably, the first mass analyzer performs the MS1 scans at a frequency of at least 0.5 Hz (scans/second), at least 1 Hz, at least 2 Hz, at least 3 Hz, or at least 4 Hz.

In a second mode of operation of the C-trap 100, ions passing through the quadrupole exit lens/split lens arrangement 80 and first transfer multipole 90 into the C-trap 100 may also continue their path through the C-trap and into the fragmentation chamber 120. As such, the C-trap effectively operates as an ion guide in the second mode of operation. Alternatively, cooled ions in the C-trap 100 may be ejected from the C-trap in an axial direction into the fragmentation chamber 120. The fragmentation chamber 120 is, in the mass spectrometer 10 of FIG. 1, a higher energy collisional dissociation (HCD) device to which a collision gas is supplied. Precursor ions arriving into the fragmentation chamber 120 collide with collision gas molecules resulting in fragmentation of the precursor ions into fragment ions.

Although an HCD fragmentation chamber 120 is shown in FIG. 1, other fragmentation devices may be employed instead, employing such methods as collision induced dissociation (CID), electron capture dissociation (ECD), electron transfer dissociation (ETD), photodissociation, and so forth.

Fragmented ions may be ejected or transmitted from the fragmentation chamber 120 at the opposing axial end to the C-trap 100. The ejected fragmented ions pass into a second transfer multipole 130. The second transfer multipole 130 guides the fragmented ions from the fragmentation chamber 120 into an extraction trap (second ion trap) 140. The extraction trap 140 is a radio frequency voltage-controlled trap containing a buffer gas. For example, a suitable buffer gas is argon at a pressure in the range 5×10−4 mBar to 1×10−2 mBar. The extraction trap has the ability to quickly switch off the applied RF voltage and apply a DC voltage to extract the trapped ions. A suitable flat plate extraction trap, also referred to as a rectilinear ion trap, is further described in U.S. Pat. No. 9,548,195 (B2). Alternatively, a C-trap may also be suitable for use as a second ion trap.

The extraction trap 140 is provided to form an ion packet of fragmented ions, prior to injection of the ion packet into the time of flight (TOF) mass analyzer 150. Alternatively, or in addition to the electrometer described above in relation to the multipole 90 and/or C-trap 100, an electrometer may be provided to measure a flow of fragmented ions into the extraction trap 140. To that end, the electrometer may sample a predefined proportion of the fragmented ions passing into the extraction trap 140. Such electrometer may be positioned between the fragmentation chamber 120 and the extraction trap 140 to sample the flow of fragmented ions passing into the extraction trap 140. Using either or each electrometer described above, the rate of flow of ions may be measured and an injection time and/or a number of pulses of fragmented ions for MS2 analysis in each precursor mass segment may be determined based on the flow of ions measured by the electrometer(s). For example, an injection time and/or a number of pulses of fragmented ions for MS2 analysis in precursor mass segments with particular intensity values (e.g. relatively higher intensity values or classes) may be determined based on the flow of ions measured by the electrometer(s) so as to analyze a predetermined number of ions (e.g. 10,000 ions) in each of those mass segments. In other precursor mass segments (e.g. mass segments with the remaining relatively lower intensity values or classes, in particular the lowest intensity class), the injection time and/or a number of pulses of fragmented ions for MS2 analysis may be a predefined time (e.g. 2 milliseconds per mass segment) or the remaining analysis time divided by the number of remaining mass segments). To form the ion packet, the extraction trap 140 accumulates fragmented ions prior to injection of the fragmented ions into the time of flight mass analyzer 150 to perform MS2 scans of the ions. Preferably, the TOF mass analyzer performs the MS2 scans at a mass resolution of at least 15,000, at least 30,000, at least 50,000, or more preferably at least 60,000, at least 75,000, at least 100,000, at least 150,000 or at least 200,000 (resolution at 200 m/z). The MS2 scans are preferably performed with 5 ppm, or better (e.g. 1-2 ppm) in mass accuracy. Preferably, the TOF mass analyzer performs the MS2 scans of the precursor mass segments at a frequency of at least 100 Hz (scans/second), at least 150 Hz, or at least 200 Hz.

The amount of fragmented ions within an ion packet of fragmented ions inside the extraction trap 140 may be controlled by controlling the injection time for accumulating the fragmented ions within the extraction trap 140. Increasing the injection time of accumulating the fragmented ions within the extraction trap 140, for example, will increase the amount of fragmented ions accumulated and thus the amount of fragmented ions in the ejected ion packet.

To that end, the injection time for accumulating fragmented ions may be calculated or determined based on an ion intensity value for the corresponding precursor mass segment as will be described in more detail in connection with the method depicted in FIG. 2.

The controller 195 is controllably connected to the mass filter 70, the C-trap 100, the mass analyzer 110, the fragmentation chamber 120, the extraction trap 140 and the second mass analyzer 150 to operate in accordance with the method of mass spectrometry described below in connection with FIG. 2. The controller 195 comprises a computer having at least one processor, as well as associated control electronics. The controller 195 controls voltages applied to these parts of the mass spectrometer. The controller 195 is interfaced to the detector of each mass analyzer 110, 150 for receiving signals from the detector in response to detecting ions. The computer of the controller processes the detector signals to produce a mass spectrum (e.g. in either MS1 or MS2 domain). The controller comprises a data storage unit (memory), which is used for example for storing data from the detector, mass spectra, etc. The computer of the controller 195 runs a computer program product, provided in software or firmware, which comprises program instructions that, when loaded into the memory and executed by one or more processors of the computer, causes the computer (and associated control electronics) to control the mass spectrometer 10 to carry out the method as described below. The computer program product comprises the computer program stored on a computer-readable medium. The controller further includes a user interface (e.g. display screen, keyboard and/or mouse) to allow a user to input information to the controller, such as a selection of a method of operation, and/or setting parameters of a method of operation (e.g. a mass range of interest, a mass resolution of the MS1 and MS2 scans, a precursor mass segment width, etc.)

Although an extraction trap (ion trap) is shown in the embodiment of FIG. 1, the skilled person will appreciate that other methods of forming an ion packet of fragmented ions will be equally suitable for the present invention. For example, relatively slow transfer of ions through a multipole can be used to affect bunching of ions, which can subsequently be ejected as a single packet to the TOF mass analyzer. Alternatively, orthogonal displacement of ions using an orthogonal accelerator may be used to form one or more ion pulses. The amount of fragmented ions may be controlled by controlling the number of ion pulses as will be described below in connection with FIG. 2 in more detail. Further details of these alternatives are found in US20030001088 A1 which describes a travelling wave ion bunching method, the contents of which are herein incorporated by reference.

In FIG. 1, the time of flight mass analyzer 150 shown is a multiple reflection time of flight mass analyzer (mr-TOF) 150. However, it will be appreciated that in other embodiments any other suitable type of TOF mass analyzer may be used instead, such as a linear TOF mass analyzer, single reflection or reflectron TOF. The mr-TOF 150 is constructed around two opposing ion mirrors 160, 162, elongated in a drift direction. The mirrors 160, 162 are opposed in a direction that is orthogonal to the drift direction. The extraction trap 140 injects ions into the first mirror 160 and the ions then oscillate between the two mirrors 160, 162. The angle of ejection of ions from the extraction trap 140 and additional deflectors 170, 172 allow control of the energy of the ions in the drift direction, such that ions are directed down the length of the mirrors 160, 162 as they oscillate, producing a zig-zag trajectory. The 30 mirrors 160, 162 themselves are tilted relative to one another, producing a potential gradient that retards the ions' drift velocity and causes them to be reflected back in the drift dimension and focused onto a detector 180. The tilting of the opposing mirrors would normally have the negative side-effect of changing the time period of ion oscillations as they travel down the drift dimension. This is corrected with a stripe electrode 190 (to act as a compensation electrode) that alters the flight potential for a portion of the inter-mirror space, varying down the length of the opposing mirrors 160, 162. The combination of the varying width of the stripe electrode 190 and variation of the distance between the mirrors 160, 162 allows the reflection and spatial focusing of ions onto the detector 180 as well as maintaining a good time focus. A suitable mr-ToF 150 for use in the present invention is further described in US 2015028197 (A1), the contents of which are hereby incorporated by reference in its entirety. It will be appreciated that alternative types of mr-TOF mass analyzer can be used in place of the elongated opposing mirrors type used in the TOF mass analyzer 150, for example a type as disclosed in U.S. Pat. No. 8,395,115 (Thermo Fisher Scientific).

In another embodiment, the MS1 mass spectrum may be acquired on the mr-ToF mass analyzer 150 instead of the first mass analyzer 110. In that embodiment, the voltage difference between the fragmentation chamber 120 and upstream component(s) of the system, including C-trap 100, are adjusted by the controller 195 such that the collision energy of the ions does not cause fragmentation in the fragmentation chamber 120 but rather unfragmented precursor ions pass from fragmentation chamber 120 into the second transfer multipole 130 and from there into the extraction trap (second ion trap) 140. Therefore, it will be appreciated that the first mass analyzer 110 may not be needed in some embodiments. A single time of flight (ToF) mass analyzer (such as mr-ToF analyzer 150), or two ToF mass analyzers (one being in place of orbital trapping mass analyzer 110), may be used instead.

Figure 2:
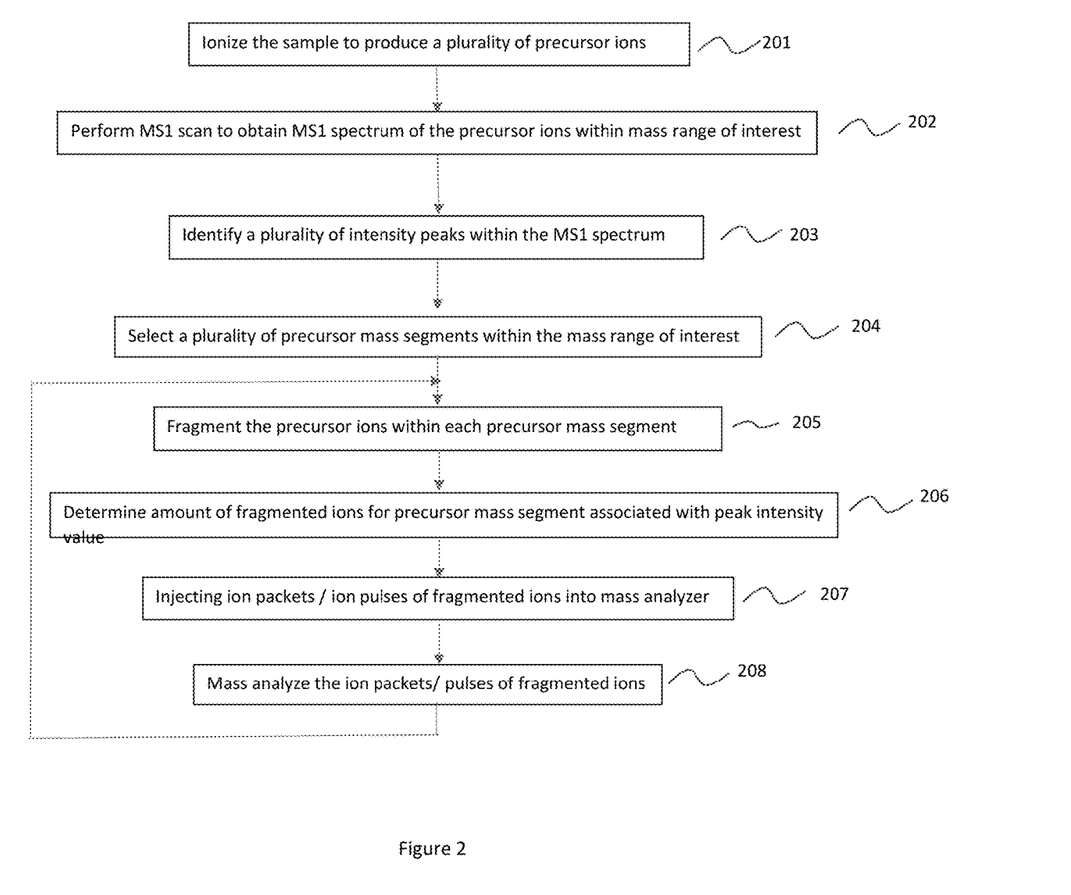
FIG. 2 shows an exemplary flow chart of a method according to an embodiment of the present invention.

FIG. 2 depicts a method of mass spectrometry of a sample within a mass range of interest according to the present teachings. The mass range of interest may be defined by the properties of the sample or defined according to the requirements of obtaining a mass spectrum. The mass range of interest is typically a wide or 'panoramic' range (e.g. having a range 400 Da or wider, 600 Da or wider, 800 Da or wider, 1000 Da or wider, etc.). The mass range of interest may be at least 20×, 40×, 60×, 80×, 100×, 200×, 300×, or 400× the width of the precursor mass segments. The method of FIG. 2 may be implemented using any of the mass spectrometers described in connection with FIG. 1, FIG. 4, or FIG. 5.

The method starts with a step 201 of ionizing the sample using ionization source 20 to produce a plurality of precursor ions. The step of ionizing the sample may be preceded by a step of separating molecules of the sample by a chromatography system and the sample may be ionized as it elutes from a chromatography system.

On the precursor ions, a precursor ion mass scan or MS1 scan (i.e. without fragmentation) is performed in step 202. This can be performed using first mass analyzer 110 (or in an alternative embodiment using mr-TOF analyzer 150). The precursor MS1 ion scan may be a panoramic scan in the sense that a complete spectrum within a certain mass range of interest is obtained. The step of performing an MS1 scan 202 includes mass analyzing the precursor ions across the mass range of interest, to obtain an MS1 mass spectrum of the precursor ions in the MS1 domain and evaluating (i.e. determining) ion intensity values across the mass range of interest in the MS1 spectrum (step 203), which may comprise identifying a plurality of intensity peaks and their intensities and/or may comprise integrating ion intensity within the MS1 spectrum, particularly within intervals of the MS1 spectrum. The identified intensity peaks may be local maxima of the MS1 spectrum and/or areas of the MS1 spectrum above a minimum intensity threshold. Each intensity peak may be identified by a pair of values: a mass (m/z) value representing the position of the center of the peak and an intensity value representing the height of the peak (and the number (i.e. intensity) of ions).

According to the method of the present teachings, a plurality of mass subranges may be selected within the mass range of interest in step 204. In one embodiment, the mass range of interest may be divided into the plurality of mass subranges. The mass range of interest may be continuous or discontinuous, e.g. comprised of a plurality of mass subranges, wherein one or more further mass subranges are excluded from the mass range of interest. The precursor mass segments can be predefined according to a DIA approach, i.e. defined before the MS1 scan is performed, or defined after the MS1 scan is performed. The controller of the mass spectrometer can define the precursor mass segments, for example in accordance with preset instructions or user input instructions. The controller can control the mass selector of the mass spectrometer to select ions in each precursor mass segment in turn, which are then fragmented and mass analyzed as described, before the mass selector is controlled to select ions in the next precursor mass segment and so on. The parameters of the precursor mass segments, i.e. their width, carries information about the range of possible sample ions within that precursor mass segments.

For each precursor mass segment, an intensity value is determined from the MS1 mass spectrum. The intensity value may be a peak intensity value and may be based on a maximum intensity value of the maximum peak within the precursor mass segment in the MS1 spectrum. The peak intensity value may be based on a peak intensity value of a single peak or an integrated or accumulated intensity value within the precursor mass segment. The intensity value for each precursor mass segment may represent a measure of the number of precursor ions detected in the MS1 spectrum in that precursor mass segment. The intensity value for the precursor mass segment may be an intensity value within the precursor mass segment or within a neighboring mass segment such as an adjacent mass segment. For example, mass subranges may be defined within the mass range of interest, each mass subrange comprising a plurality of neighboring precursor mass segments such that all precursor mass segments within the mass subrange are assigned to the same intensity value.

The plurality of precursor mass segments may or may not have substantially the same mass range. Preferably, however, the plurality of precursor mass segments have substantially the same mass range. The mass range of the precursor mass segments may be 20 Da (Dalton) or less, 15 Da (Dalton) or less, 10 Da (Dalton) or less, 8 Da (Dalton) or less, 6 Da (Dalton) or less, 4 Da (Dalton) or less, 3 Da (Dalton) or less, or 2 Da (Dalton) or less.

The plurality of precursor mass segments typically span across the whole of the mass range of interest. The identified precursor mass segments may be arranged on a common mass segment grid, such that mass segments may be adjacent to each other and non-overlapping. Alternatively, the mass segments may be overlapping and/or be placed or centered around an identified peak. Each precursor mass segment may or may not comprise one or a plurality of identified peaks.

The method proceeds with a step of performing one or more MS2 scans or fragmented ion scans, each MS2 scan or fragmented ion scan being performed for a corresponding precursor mass segment. The ions in each precursor mass segment can be selected using the mass selector 70.

For each MS2 scan, the selected precursor ions within each precursor mass segment are fragmented into a group of fragmented ions 205. The precursor ions within each precursor mass segment can be fragmented in the fragmentation chamber 120.

For each MS2 scan of the fragmented ions, an amount of fragmented ions or ions to be fragmented for that precursor mass segment is determined in step 206, wherein control of the amount of fragmented ions or ions to be fragmented is based on the intensity value determined previously for that precursor mass segment. The amount of fragmented ions may be based on a peak intensity value, or, if no peak has been identified for that precursor mass segment, may be a default value (which may be a lowest value) or integrated intensity value. The determining step 206 may be performed before or after fragmenting the precursor ions within the precursor mass segment.

The amount of fragmented ions is converted into an ion packet or one or more ion pulses and supplied to a mass analyzer for performing an MS2 scan 207 to mass analyze the fragmented ions 208. The TOF mass analyzer 150 can be used for performing the MS2 scans. The amount of fragmented ions comprises the ion packet or the one or more ion pulses.

The amount of ions may be controlled by controlling the injection time of the fragmented ions into an extraction trap, such as extraction trap 140 in FIG. 1, where they accumulate prior to being supplied to the mass analyzer as an ion packet. To that end an ion packet from the fragmented ions may be accumulated within an extraction trap before mass analysis in a mass analyzer. Performing the MS2 scan may then include ejecting the ion packet from the extraction trap into a mass analyzer for performing the MS2 scan.

For example, the injection time into the extraction trap may be determined, such that a total charge or a number of fragmented ions is substantially equal for the ion packets of fragmented ions generated for each of the precursor mass segments.

Alternatively, the amount of ions may be controlled by controlling the number of pulses generated from the fragmented ions within the precursor mass segment by an injector, preferably an orthogonal accelerator injector, wherein the pulses generated by the injector are injected by the injector into a time-of-flight mass analyzer for generating the MS2 scan/fragmented ion scan. Each pulse into the time-of-flight mass analyzer yields an individual MS2 scan, and the individual MS2 scan are then added together to provide the MS2 scan for that precursor mass segment.

The method described above relies on a step of using an intensity value determined in the MS1 domain to control an amount of fragmented ions to be analyzed for performing an MS2 scan of a precursor mass segment.

Over the mass range of interest, the intensity of the precursor ions can vary by up to several orders of magnitude. This creates the problem that when a fixed ion injection time or fixed number of ion pulses is used for the MS2 scans, peaks in the MS2 scans for some of the precursor mass segments may saturate the detector, while peaks in some other precursor mass segments may not be recorded. Ion populations with low ion numbers in some precursor mass segments can be particularly under-represented due to the low intensities they have. The present invention addresses this by adjusting the number of fragmented ions in each precursor mass segment for the MS2 scans, for example by adjusting an ion injection time or number of ion pulses used based on the intensity value determined from the MS1 mass spectrum for that precursor mass segment. In this way, for the MS2 scans, precursor mass segments corresponding to lower intensity in the MS1 mass spectrum use a longer ion injection time or higher number of ion pulses for their fragmented ions compared to precursor mass segments corresponding to higher intensity in the MS1 mass spectrum. The amounts of fragmented ions to be analyzed for performing the MS2 scans can thereby be controlled to be more equal in the different precursor mass segments, preferably to be substantially the same. In one embodiment, in order to use ion intensity values for control of amounts of fragmented ions, a plurality of intensity classes may be defined for the intensity values, wherein similar intensity values, or intensity values within a defined range, are grouped into a common intensity class and given a common intensity value for that class. Each precursor mass segment may then be assigned to one of the plurality of intensity classes, and the amount of fragmented ions may be determined or controlled based on the assigned intensity class, e.g. such that each intensity class may be used to determine an injection time of ions into an extraction trap, or determine a number of pulses from an orthogonal accelerator injector, for MS2 scans in a TOF mass analyzer, associated with a fixed amount of fragmented ions or ions to be fragmented.

The precursor mass segments have to be processed in a certain order by the mass spectrometer for performing the MS2 scans. To that end, an order of processing the precursor mass segments may be defined for the intensity classes. In one such embodiment, a precursor mass segment assigned to an intensity class associated with a higher peak intensity is processed earlier or before a precursor mass segment assigned to an intensity class associated with a lower peak intensity, which may be processed later. In another embodiment, an opposite order of processing to this may be employed. To that end all precursor mass segments within the mass range of interest may be processed, or only those precursor mass segments that have higher ranking intensity values may be processed, or only those precursor mass segments that have lower ranking intensity values may be processed. If required, one or more precursor mass segments can be skipped (omitted) from the sequence of MS2 scans, for example if any such mass segment has been placed in an exclusion list. A mass segment may be placed in an exclusion list, for example, based on an earlier mass analysis of that mass segment.

Neighboring precursor mass segments within the mass range of interest may be grouped into a common mass subrange, such that all the precursor mass segments within the mass subrange are assigned to the same amount of fragmented ions for mass analysis within the MS2 domain. Accordingly, all the precursor mass segments within a mass subrange may be assigned to the same intensity value, e.g. an intensity class that represents the intensity range for that mass subrange. Thus, a plurality of mass subranges can be defined within the mass range of interest, each mass subrange comprising a plurality of neighboring precursor mass segments grouped based on their intensity values.

The amount of ions may be controlled by controlling the injection time of the fragmented ions accumulated within an extraction trap as an ion packet, and ejecting the ion packet from the extraction trap into a mass spectrometer for performing the MS2 scan.

Alternatively, the amount of ions may be controlled by controlling the number of ion pulses generated from the fragmented ions within the precursor mass segment by an orthogonal accelerator injector and injected into a time-of-flight mass spectrometer for performing the MS2 scan.

In the methods of mass spectrometry described above, for performing the MS1 scan and for performing the MS2 scan the same mass analyzer may be used, wherein preferably the mass analyzer for performing an MS1 scan and also subsequently performing an MS2 scan may be a time-of-flight mass analyzer.

Alternatively, in the methods of mass spectrometry described above, the MS1 scan may be performed using a first mass analyzer operating according to a first mass analysis principle, and the MS2 scan may be performed using a second mass analyzer operating according to a second mass analysis principle. For example, the first mass analyzer may be a Fourier transform mass analyzer, such as an Orbitrap mass analyzer, and the second mass analyzer may be a time-of-flight mass analyzer, such as a multi-reflection time-of-flight mass analyzer.

Figure 3:
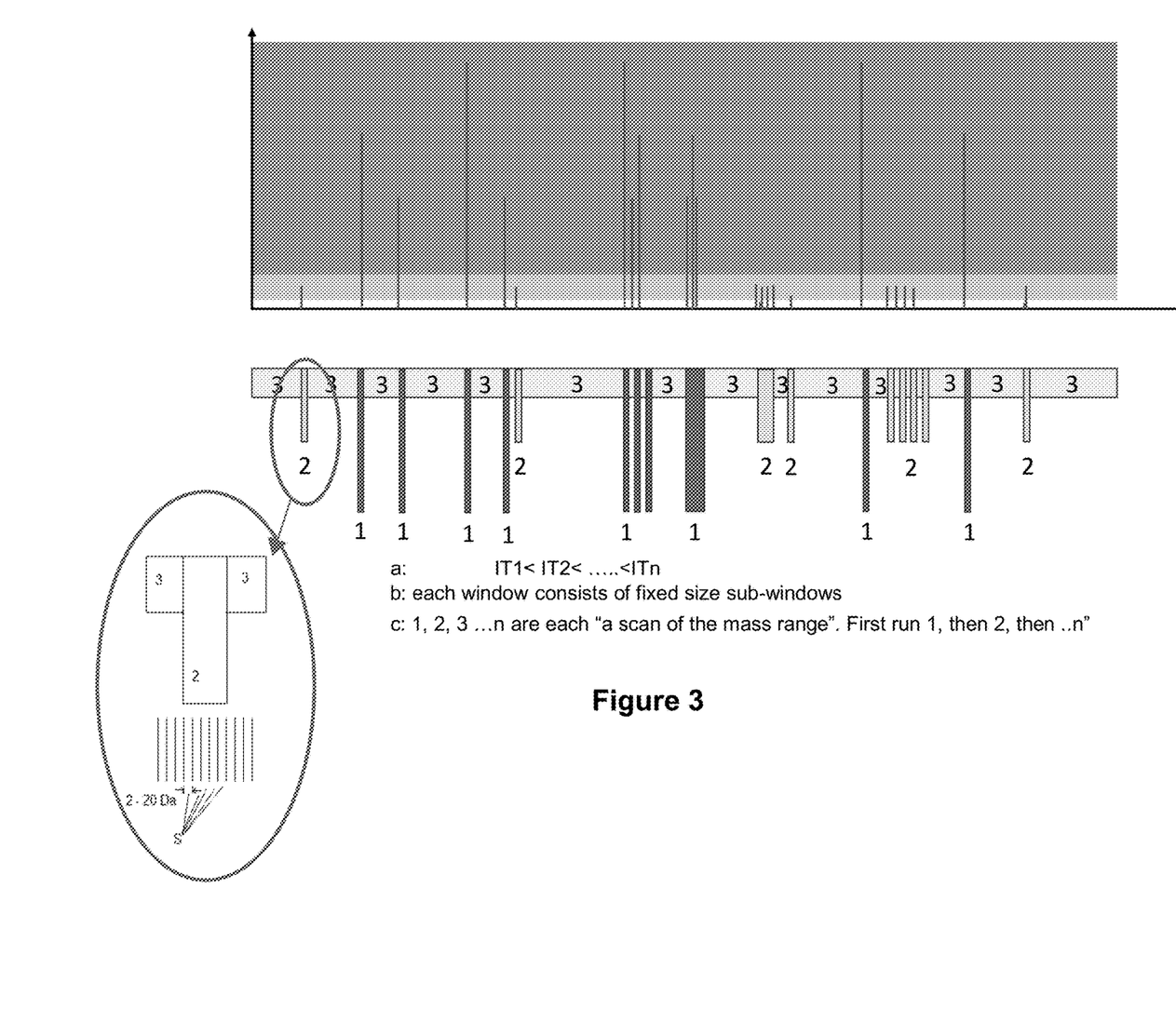
FIG. 3 shows an exemplary diagram of an MS1 spectrum and mass subranges within the MS1 spectrum for analysis according to an embodiment of the present invention.

FIG. 3 depicts a schematic mass spectrum from an MS1 scan of precursor ions of a sample (wherein the horizontal axis represents m/z and the vertical axis represents ion intensity) on the upper half of the figure and on the lower half a grouping of precursor mass segments into mass subranges that is applied for subsequently performing MS2 scans on the fragmented ions obtained by fragmenting precursor ions within the respective precursor ion mass segments.

The MS1 scan may be performed, for example, using a Fourier transform mass analyzer or using a time-of-flight mass analyzer as shown in FIG. 1. The MS1 scan may be obtained as a full spectrum (survey spectrum) acquired using a fixed total number of ions or fixed injection time for accumulating the ions for the MS1 scan. On a time of flight mass analyzer, the acquisition time of the MS1 scan may be in the order of a few microseconds or may be longer or shorter than a few microseconds. The acquisition time is typically longer than this for a high resolution MS1 scan using a Fourier transform mass analyzer.

The mass spectrum from the MS1 scan indicates areas of the spectrum having peaks of high intensity, lower intensity and areas with no observable peaks at all. The MS1 mass spectrum comprises a plurality of intensity peaks, which may be grouped into peak intensity classes. Each intensity class covers a range of intensity of values. Any number of intensity classes may be defined. In the MS1 scan depicted on the upper half of FIG. 3, three intensity classes are defined, which are depicted as a dark grey band indicating high intensity peaks, a medium grey band indicating medium intensity peaks and a white band indicating that no peaks or no peaks above a predefined threshold are present (low intensity). It will be appreciated that more than three intensity classes may be employed in other embodiments.

In the lower half of FIG. 3, the precursor mass spectrum is depicted as being divided into mass subranges according to the peak intensities (i.e. intensity classes) present in the MS1 scan. Mass subranges comprising high intensity peaks are marked or classified as intensity class "1", mass subranges comprising medium intensity peaks are marked or classified as intensity class "2". Further mass subranges between the mass segments depicted as "1" and the mass subranges depicted as "2", i.e. mass subranges in which no peaks have been identified or that do not comprise peaks above a certain threshold are depicted as intensity class "3".

The mass subranges having the high intensity peaks (classified as intensity class "1") are typically relatively narrow. These mass subranges are divided into a plurality of narrower precursor mass segments, preferably each of a fixed 2-20 Da width or less (preferably 2 Da or less). The precursor mass segments in these mass subranges have the shortest injection time or lowest number of pulses for their fragmented ions.

The mass subranges having the lower (maximum) intensity peaks (classified as intensity class "2") are typically wider than the high intensity subranges. These mass subranges are also divided into a plurality of narrower precursor mass segments, preferably each of a fixed 2-20 Da width or less (preferably 2 Da or less). The precursor mass segments in these mass subranges have a longer injection time or higher number of pulses for their fragmented ions than the precursor mass segments in the high intensity mass subranges.

The process is repeated for mass subranges having even lower intensity peaks (e.g. intensity classes "3", "4", . . . , "n"). The final mass subranges having no visible peaks or only peaks below a certain threshold are denoted "n". In FIG. 3, it shows these mass subranges having no visible peaks or only peaks below a certain threshold denoted as "3". Once again, these mass subranges are also divided into a plurality of narrower precursor mass segments, preferably each of a fixed 2-20 Da width or less (preferably 2 Da or less). The precursor mass segments in these mass subranges preferably have the longest injection time or highest number of pulses for their fragmented ions.

In some embodiments, instead of, or in addition to, using the maximum peak intensity in a mass subrange to classify the subrange, it is possible to use an integrated intensity within the mass subrange. Accordingly, in some embodiments, the method may comprise identifying a first set ("1") of one or more mass subranges within the mass range of interest based on the MS1 spectrum, wherein each of the one or more mass subranges in the first set includes one or more peaks, or an integrated intensity, in the MS1 spectrum having an intensity that is above a first intensity threshold (corresponding to intensity class 1). The method may further comprise identifying a second set ("2") of one or more mass subranges within the mass range of interest based on the MS1 spectrum, wherein each of the one or more mass subranges of the second set does not include one or more peaks, or an integrated intensity, in the MS1 spectrum having an intensity that is above the first intensity threshold. In such case, the one or more mass subranges of the second set may include one or peaks above a second intensity threshold (corresponding to intensity class 2). The method may still further comprise identifying a third set ("3") of one or more mass subranges (corresponding to intensity class 3) within the mass range of interest based on the MS1 spectrum, wherein each of the one or more mass subranges of the third set does not include one or more peaks having an intensity that is above the second intensity threshold. In some embodiments, more than three sets of mass subranges (corresponding to separate intensity classes) may be used. Thus, embodiments may further comprise identifying n further sets of one or more mass subranges based on the MS1 spectrum (n is an integer). Generally, in an $i^{th}$ set of mass subranges, each subrange includes one or more peaks, or an integrated intensity, having an intensity that is above an $i^{th}$ intensity threshold but does not include one or more peaks, or an integrated intensity, above an $(i-1)^{th}$ intensity threshold. Preferably, the widths of the mass subranges are: width of mass subrange 1<width of mass subrange 2<width of mass subrange 3<width of mass subrange n.

The mass range of interest is divided into a sequence of narrow precursor mass segments for the MS2 scans. The mass subranges labelled with intensity classes 1, 2 and 3 each comprise a plurality of the precursor mass segments, a number of which are labelled "s" in the enlarged view of the first three mass subranges on the left hand side of the lower half of FIG. 3. The precursor mass segments generally have a fixed width, which can be in the range 2-20 Da, or even lower, or even higher, as described further below. The depicted precursor mass segments are adjacent to each other and non-overlapping. The precursor mass segments may be arranged on a common mass segment grid. Alternatively, the mass segments may be overlapping and/or be placed or centered around an identified peak. Each precursor mass segment comprising identified peaks may comprise one or a plurality of identified peaks. The precursor mass segments may or may not have the same or substantially the same mass range width. In some embodiments, the precursor mass segments have the same or substantially the same mass range width (herein a 'fixed' width). The mass range width of the precursor mass segments may be preset, e.g. by the controller of the mass spectrometer. The mass range width may be 20 Da (Dalton) or less, 15 Da (Dalton) or less, 10 Da (Dalton) or less, 8 Da (Dalton) or less, 6 Da (Dalton) or less, 4 Da (Dalton) or less, 3 Da (Dalton) or less, or 2 Da (Dalton) or less. In some embodiments, the precursor mass segments are defined as having a fixed width (e.g. a fixed width in the range 20 Da to 2 Da or less) and collectively cover the mass range of interest. For example, an 800 Da wide mass range of interest from 400-1200 (Da or m/z) could be divided into 200 sequential 4 Da wide precursor mass segments (400-404 Da, 404-408 Da, 408-412 Da, . . . , 1196-1200 Da). Alternatively, such mass range of interest could be divided into 400 precursor mass segments of 2 Da width, or divided into 100 precursor mass segments of 8 Da width, or divided into 40 precursor mass segments of 20 Da width etc. The use of narrower mass segment widths (e.g. about 2 Da or less) may enable a database search to be used as an alternative or addition to use of spectral libraries to identify the molecular species in the sample.

For each precursor mass segment, the precursor ions of that mass segment are fragmented in one fragmentation step (such as in fragmentation chamber 120 of FIG. 1) and the fragmented ions are processed to obtain an MS2 spectrum of the fragmented ions stemming from that particular precursor mass segment.

To that end a peak intensity value of a precursor mass segment in the MS1 scan is converted into an amount of fragmented ions or ions to be fragmented, analyzed to obtain an MS2 scan of the fragmented ions. To that end, an amount of fragmented ions may be determined based on the peak intensity classes described above.

The amount of ions may be controlled by controlling an injection time for accumulating an ion packet of fragmented ions or by controlling a number of ion pulses of fragmented ions.

If the injection time for accumulating an ion packet is controlled, that injection time IT may be determined using the following approach:

Determine a fixed injection time IT for precursor mass segments separately in each of the mass subranges ("1", to "n−1"), wherein the injection time is lower for the high intensity mass subranges: IT1<IT2< . . . <ITn−1. Suitable injection times may be determined by calibration or from a previous experiment. The fixed injections times for each of the mass subranges may be determined to provide a suitable number of ions for the MS2 scans (e.g. not saturating the detector but providing a measurable intensity). The remaining mass subranges "n" may utilize the remaining acquisition time for MS2 scans divided by the number of the remaining precursor mass segments (e.g. 2-20 Da width segments) in those mass subranges "n" as the injection time. This follows from the feature that there is generally a maximum or defined amount of time for a DIA cycle (i.e. the cycle comprising the full set of MS2 scans across the mass range of interest) in order to allow enough sampling points over a chromatographic peak. Therefore, it is advantageous to maximise the IT available for the lower intensity regions. Thus, the invention may enable the dynamic range of the DIA analysis to be improved by spending different (longer) amounts of time on parts of the mass spectrum with lower intensity.

A cycle time of a DIA method according to the invention preferably substantially consists of the time to perform the MS1 scan and the full set of MS2 scans (i.e. for all precursor mass segments in the mass range of interest). The DIA cycle is preferably performed at least 2 times, or 3 times, or 4 times, or 5 times, or 6 times, or 7 times, or 8 times over the width of a chromatographic peak (width at peak base). A single DIA cycle may take 1-5 seconds (e.g. 2-4, or ~3 seconds).

Alternatively, injection times IT may be determined using a fixed injection time IT for each of the mass subranges ("1" to "n"), i.e. a fixed injection time for all subranges, wherein the injection time is lower for the high intensity mass subranges: $IT_1 < IT_2 < \ldots < IT_n$.

The processing of the precursor mass segments by the mass spectrometer for performing the MS2 scans may be initiated by first processing the precursor mass segments within the mass subranges of high intensity ("1") and then continuing with processing the precursor mass segments within the mass subranges of next highest intensity ("2") until the mass subranges of lowest intensity ("n").

Using the method according to the present teachings enables a data independent acquisition of mass spectra in the form of a set of MS2 mass spectra for the precursor mass segments across the mass range of interest, in addition to an MS1 mass spectrum of the mass range of interest. Information on precursor ion masses derived from peaks identified in the MS1 mass spectrum and information on corresponding fragment ion masses from peaks identified in the MS2 mass spectra can be used with a database search or spectral library to identify precursor molecular species present in the sample. Using narrow (e.g. 2 Da or less) precursor mass segments, it may be possible to use a database search with or without the MS1 peak information. In one approach, an MS1 spectrum acquired at high resolution and high mass accuracy, as described above, can be used to produce a precursor ion candidate list using a standard non-fragment ion-database. In-silico fragmentation of the candidates in the list can produce within the narrow mass range a library against which fragmentation spectra are compared and/or quantified as known in the art in order to provide identification of the precursor ions.

Figure 4:
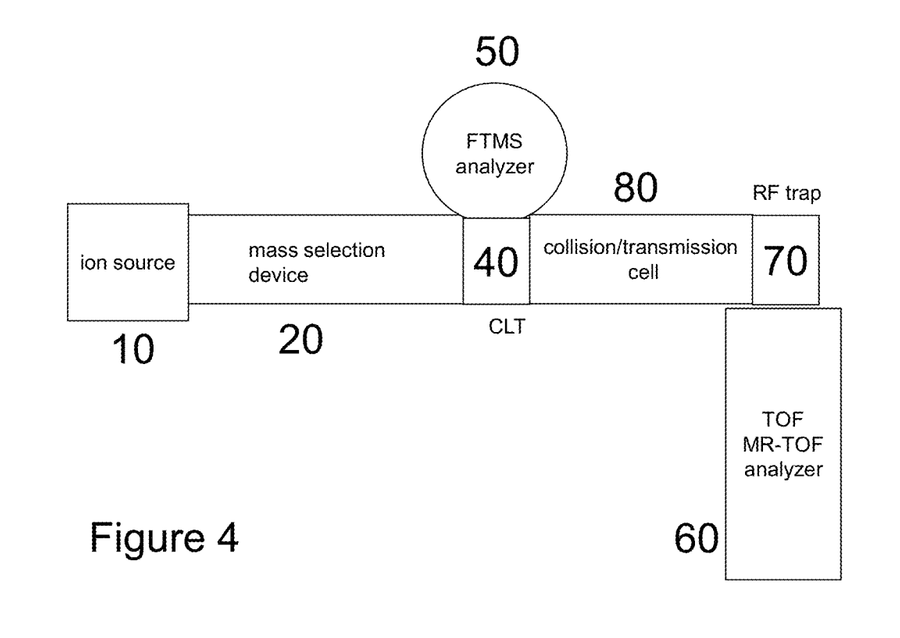
FIG. 4 shows a schematic diagram of an alternative mass spectrometer suitable for carrying out a method in accordance with an embodiment of the present invention.

An alternative embodiment of a mass spectrometer suitable for use in connection with a method embodying the present invention is shown schematically in FIG. 4. In the embodiment of FIG. 4, an ion source 10 is coupled to a mass selection device 20. Such an arrangement may be provided by the ESI ion source 20 and its respective couplings to the quadrupole mass filter 70 as shown in the embodiment of FIG. 1. As shown in FIG. 4, the output of the mass selection device 20 is coupled to a C-trap (curved linear ion trap) 40. In a first mode of operation, precursor ions may be collected in the C-trap 40 for subsequent emission into the mass analyzer 50 for performing an MS1 scan. The MS1 scan may be analyzed with respect to the identification of intensity peaks and/or the identification and classification of mass subranges as described above in relation to the method of FIG. 2 and FIG. 3. The mass analyzer 50 may be a Fourier Transform mass spectrum (FTMS) analyzer 50, which may be embodied as an orbital trapping mass analyzer, a Fourier Transform Ion Cyclotron Resonance (FTICR) mass analyzer or any other type of Fourier Transform mass analyzer. Mass analyzers, such as the orbital trapping mass analyzer and Ion Cyclotron Resonance mass analyzer, may also be used in the invention even where other types of signal processing than Fourier transformation are used to obtain mass spectral information from the transient signal (see for example WO 2013/171313, Thermo Fisher Scientific).

According to a second mode of operation, precursor ions are transmitted by the C-trap 40 further to the fragmentation chamber 80, such as a collision/transmission cell etc., where they are fragmented. The mass range of the precursor ions to be transmitted to the transmission/collision cell 80 may be selected in accordance with a method described above in relation to FIG. 2 and FIG. 3. The fragmented ions are subsequently accumulated in the RF (radio frequency controlled) trap 70, wherein the injection time for accumulating the fragmented ions may be controlled in accordance with the method described above in connection with FIGS. 2 and 3. A packet of fragmented ions accumulated in the RF trap 70 is subsequently ejected into the mass analyzer 70 for performing an MS2 scan, which may be embodied as a time-of-flight mass analyzer, such as multi-reflection time-of-flight mass analyzer.

Figure 5:
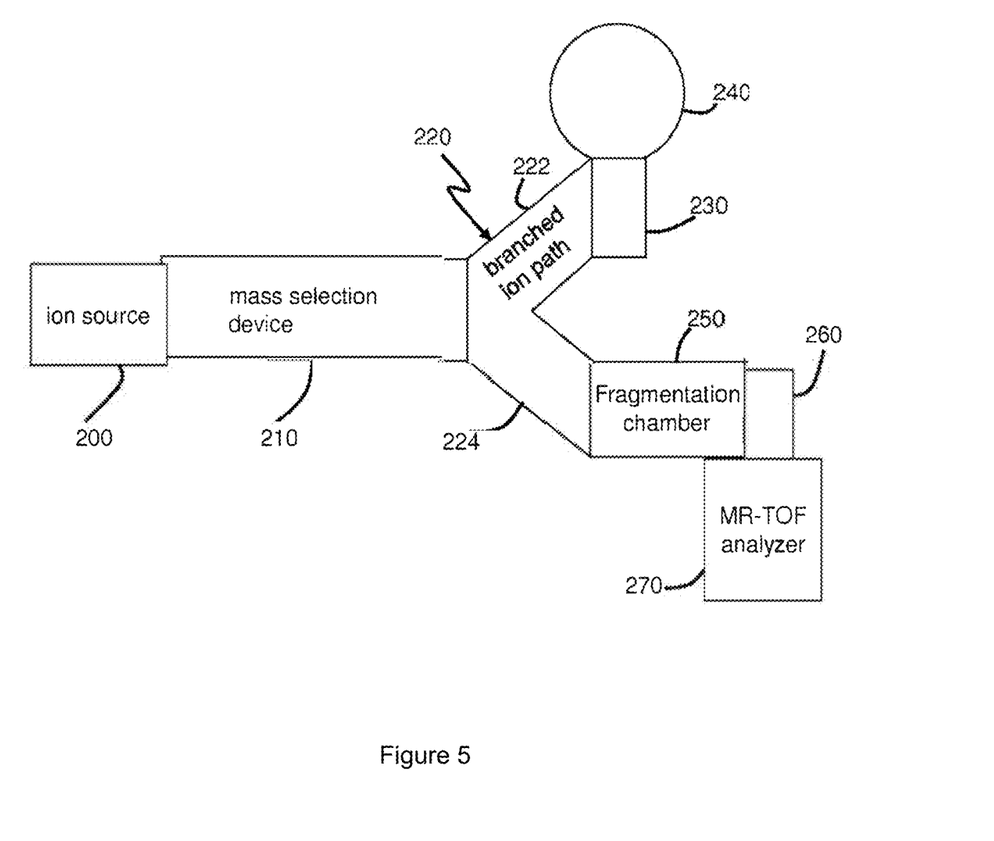
FIG. 5 shows a schematic diagram of a further alternative mass spectrometer suitable for carrying out a method in accordance with an embodiment of the present invention.

In a further alternative embodiment, the mass spectrometer according to the present invention may be provided in a branched path arrangement, for example as shown in the embodiment in FIG. 5. In the embodiment of FIG. 5, an ion source 200 is coupled to a mass selection device 210. Such an arrangement may be provided by the ESI ion source 200 and its respective couplings to the quadrupole mass filter 70 as shown in the embodiment of FIG. 1 for example. As shown in FIG. 5, the output of the mass selection device 210 is coupled to the branched ion path 220. The branched ion path directs ions output from the mass selection device along one of two paths. A first path 222 directs ions to a C-trap 230 where ions are collected for analysis by a Fourier Transform mass analyzer, for example an orbital trapping mass analyzer 240 in the MS1 domain to obtain an MS1 scan. The MS1 scan may be analyzed with respect to the identification of intensity peaks and/or the identification and classification of mass subranges as described above in relation to the method of FIG. 2 and FIG. 3. A second path 224 directs ions to a fragmentation chamber 250 for fragmentation of ions and subsequent mass analysis in the MS2 domain. The branched ion path may use an RF voltage to direction ions down either the first path 222 or the second path 224. The branched ion path may be a branched RF multipole. A branched ion path suitable for use in the embodiment of FIG. 5 is further described in U.S. Pat. No. 7,420,161.

According to the alternative embodiment in FIG. 5, the branched ion path may be used to direct ions to a C-trap 230 for MS1 analysis or to a fragmentation chamber 250 for MS2 analysis. Fragmented ions ejected from the fragmentation chamber 250 may be accumulated in ion extraction trap 260, before being injected into mr-TOF analyzer 270 as a packet. The injection time for accumulating packets of fragmented ions in the ion extraction trap 260 may be controlled in accordance with a method described above in relation to FIG. 2 and FIG. 3. As such, the arrangement of the fragmentation chamber 250, ion trap 260 and mr-TOF 270 may be provided by a similar arrangement as described in FIG. 1.

Thus, according to the alternative embodiment in FIG. 5, ions may be directed for MS2 analysis without requiring the C-trap 230 supplying the MS1 orbital trapping mass analyzer 240 to be empty. Such a configuration may allow increased parallelization of the MS1 and MS2 scans. As such, a greater proportion of the duration of a chromatographic peak may be available for carrying out MS2 scans.

By utilizing the branched path arrangement, the C-trap 230 is no longer in the path of the supply of ions to the fragmentation chamber for performing the MS2 scans. Accordingly, the C-trap 230 according to the branched path embodiment may be loaded over an extended time period using a plurality of smaller filling steps. This enables the ions accumulated in the C-trap 230 to be more representative of the chromatographic peak.

Figure 6:
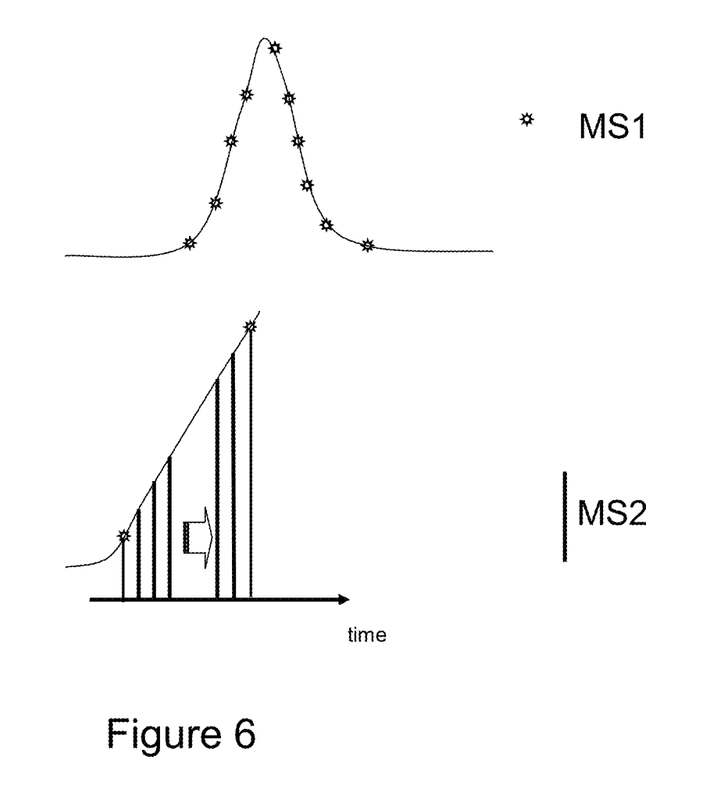
FIG. 6 shows an example of the methodology of the present disclosure according to an embodiment of the present invention superimposed onto the characteristics of a chromatographic peak.

FIG. 6 shows in the upper drawing a representation of a chromatographic peak of a sample as it elutes from a chromatographic apparatus. The points superimposed on the peak represent an example of time periods in which an MS1 scan is started. The lower drawing shows an expanded section of the chromatographic peak, wherein the vertical lines are representative of time periods in which individual MS2 scans on precursor mass segments are performed.

The invention claimed is:

1. A method of mass spectrometry for analyzing a sample within a mass range of interest, comprising the steps:
   ionizing the sample to produce a plurality of precursor ions;
   performing an MS1 scan of the precursor ions comprising mass analyzing the precursor ions across the mass range of interest, to obtain an MS1 mass spectrum of the precursor ions;
   determining ion intensity values within the MS1 mass spectrum;
   selecting precursor mass segments within the mass range of interest, each precursor mass segment having a mass range, and for each precursor mass segment:
fragmenting the precursor ions within that precursor mass segment; and
performing an MS2 scan of the fragmented ions by:
   controlling an amount of fragmented ions for that precursor mass segment, based on an intensity value for that precursor mass segment derived from the MS1 spectrum; and
   mass analyzing the amount of fragmented ions.

2. Method according to claim 1, wherein the amount of fragmented ions is controlled by controlling the injection time of the fragmented ions for accumulating an ion packet from the fragmented ions within an extraction trap and wherein performing the MS2 scan includes ejecting the ion packet from the extraction trap into a mass analyzer for performing the MS2 scan.

3. Method according to claim 2, wherein the injection time is determined, such that a total charge or a number of fragmented ions is substantially equal for ion packets of each of the precursor mass segments.

4. Method according to claim 1, wherein the amount of ions is controlled by controlling the number of pulses generated from the fragmented ions within the precursor mass segment by an ion injector, preferably an orthogonal accelerator injector, the pulses being injected by the ion injector into a time-of-flight mass analyzer for generating the MS2 scan.

5. Method according to claim 1, wherein a plurality of intensity classes are defined for the intensity values, and wherein each of the precursor mass segments is assigned to one of the plurality of intensity classes, and wherein the amount of fragmented ions is controlled based on the assigned intensity class.

6. Method according to claim 5, wherein an order of processing the precursor mass segments is defined based on the intensity classes, preferably such that a precursor mass segment assigned to an intensity class associated with a higher intensity value is processed before a precursor mass segment assigned to an intensity class associated with a lower intensity value.

7. Method according to claim 1, wherein a plurality of mass subranges, each mass subrange comprising a plurality of neighboring precursor mass segments, are defined within the mass range of interest, such that all the precursor mass segments within a mass subrange are assigned to the same intensity value.

8. Method according to claim 1, wherein intensity peaks are identified within the mass range of interest and wherein the intensity values comprise peak intensity values of the identified intensity peaks.

9. Method according to claim 1, wherein each of the plurality of precursor mass segments has substantially the same mass range.

10. Method according to claim 1, wherein the precursor mass segments comprise precursor mass segments that are adjacent to each other and non-overlapping.

11. Method according to claim 1, wherein mass ranges of precursor mass segments are overlapping.

12. Method according to claim 1, wherein for performing the MS1 scan and for performing the MS2 scan the same mass analyzer is used.

13. Method according to claim 1, wherein the MS1 scan is performed using a first mass analyzer, and wherein the MS2 scan is performed using a second mass analyzer.

14. Computer program product comprising program instructions that cause a controller of a mass spectrometer to perform the method of claim 1 when loaded into a memory of the controller.

15. A mass spectrometer for performing mass spectrometry on a sample across a mass range of interest, the mass spectrometer comprising:
   an ionization source for producing a plurality of precursor ions from the sample provided by a chromatography system;
   a mass selector for selecting a mass range of the precursor ions;
   a mass analyzer for performing an MS1 scan of the precursor ions in the MS1 domain;
   a fragmentation apparatus;
   a mass analyzer for performing an MS2 scan of fragmented ions in the MS2 domain;
   an ion packet or ion pulse forming apparatus;
   and a controller configured to:
   (i) cause the mass selector to select precursor ions within the mass range of interest,
   (ii) cause the mass analyzer for performing an MS1 scan to perform an MS1 scan of the precursor ions within the mass range of interest to obtain a MS1 spectrum of the precursor ions in the MS1 domain,
   (iii) determine ion intensity values within the MS1 spectrum,
   (iv) cause the mass selector to select within the mass range of interest a plurality of precursor mass segments, each precursor mass segment having a mass range,
   (v) control an amount of fragmented ions for each precursor mass segment, based on an intensity value for that precursor mass segment derived from the MS1 spectrum,
   (vi) cause the fragmentation apparatus to fragment the precursor ions within each precursor mass segment,
   (vii) cause the ion packet or ion pulse forming apparatus to form the amount of fragmented ions as one or more ion packets or ion pulses and to inject the ion packets or ion pulses of fragmented ions into the mass analyzer for performing an MS2 scan, (viii) cause the mass analyzer for performing an MS2 scan to mass analyze the amount of fragmented ions of the one or more ion packets or ion pulses.

\* \* \* \* \*